United States Patent [19]

Kromer et al.

[11] Patent Number: 5,088,173
[45] Date of Patent: Feb. 18, 1992

[54] ONE-TIME-USE PRECISION-BLADE-BENDING SCALPEL BLADE REMOVER-RECEPTACLE

[76] Inventors: Martin W. Kromer, 12308 Holland Rd., Poway, Calif. 92064; William W. Seneski, 13075 Wimberly Sq., #90, San Diego, Calif. 92128

[21] Appl. No.: 536,936

[22] Filed: Jun. 12, 1990

Related U.S. Application Data

[63] Continuation of Ser. No. 343,926, Apr. 26, 1989, abandoned.

[51] Int. Cl.⁵ .................... B23P 19/04; B65D 83/00; B65D 25/00; B65F 7/00
[52] U.S. Cl. .......................................... 29/239; 29/278; 206/355; 206/359
[58] Field of Search ............ 29/239, 278, 426.2, 29/426.4, 426.5; 206/355, 356, 359, 366

[56] References Cited

U.S. PATENT DOCUMENTS

| | | | |
|---|---|---|---|
| 4,120,397 | 10/1978 | Neumann | 206/356 X |
| 4,344,532 | 8/1982 | Eldridge, Jr. et al. | 206/355 X |
| 4,378,624 | 4/1983 | Klingenberg | 29/239 |
| 4,730,376 | 3/1988 | Yamada | 29/239 |
| 4,746,016 | 5/1988 | Pollak et al. | 206/356 |

FOREIGN PATENT DOCUMENTS 1596199  8/1981  United Kingdom ............ 29/239

*Primary Examiner*—Joseph M. Gorski
*Attorney, Agent, or Firm*—William C. Fuess

[57] ABSTRACT

A remover-receptacle device bends a scalpel blade having a central longitudinal aperture presenting detents from its mounted position on the tang of a scalpel blade handle so as to remove the blade from the handle. In the removal the distal, balde-end region of the scalpel blade is held completely planar from a position proximal of the detents while only the scalpel blade's proximal, shank-end region is bent. The scalpel handle's tang may thusly be slid from the scalpel blade's aperture with essentially zero removal force. The act of removing the scalpel blade locks the scalpel blade remover-receptacle shut with exactly one scalpel blade, visible through a viewing aperture, present therein. Both the one-time-use scalpel blade remover-receptacle and the single removed scalpel blade encapsulated therein may be safety transported and disposed.

2 Claims, 3 Drawing Sheets

ONE-TIME-USE PRECISION-BLADE-BENDING SCALPEL BLADE REMOVER-RECEPTACLE

This is a continuation of application Ser. No. 07/343,926 filed on Apr. 26, 1989 and now abandoned.

BACKGROUND OF THE INVENTION

1. Field of the Invention

The present invention relates generally to tools, receptacles, containers, and like systems directed to removing, used disposable surgical scalpel blades from scalpel handles and safely disposing of such contaminated blades.

2. Background of the Invention

Modern surgical scalpel blades are disposable, and fit to a reusable handle to thereby form a surgical knife. A typical commercially available surgical, or scalpel, blade has a sharpened tip and cutting edge at the forward portion of the blade and a shank extending to the rear portion of the blade. The scalpel blade has a variable width elongated central aperture, or slot, with its wider portion near the rear, or shank, and its narrower portion forward, near the blade. The shoulders of the central aperture between its wider and narrow portions act as detents.

The scalpel handle has an elongated boss, or tang, that is inserted into the aperture of the scalpel blade in order to mate with the blade and hold it during use of the surgical knife. The tang has a region of reduced thickness, and a forward-facing shoulder to this region, at its rear portion where it attaches to the scalpel handle. The front of the tang is typically rounded, and the shoulder of the reduced-thickness region is also typically rounded. The tang presents a groove on both sides.

In order to mount a scalpel blade, the front end of the tang is inserted into the wide part of the scalpel blade slot and the narrow portion of the scalpel blade slot slides in the tang's grooves until the rear of the scalpel blade's slot clears the rear of the shoulder of the reduced thickness region of the tang. The scalpel blade can then flatten, or snap, over the shoulder of the rear portion of the tang, locking the blade to the scalpel handle. In this position the rear of the scalpel blade slot is held by the shoulder on the reduced thickness region of the rear portion of the tang, which shoulder thus serves as a blade-retaining projection. The scalpel blade is held from moving further backwards on the tang by its aperture's detents, which engage a complementary feature on the tang.

To remove the scalpel blade from the scalpel handle's tang, the rear edge of the blade must be lifted away from the tang's shoulder so as to permit the handle to be drawn away from the scalpel blade. The tang must be withdrawn from the scalpel blade so that the groove, or undercut, portion of the tang becomes disengaged from the narrow portion of the scalpel blade's aperture.

The removal of a scalpel blade from a scalpel handle is problemsome, whether performed with general or specialized tools. A problem is presented when the rear, or shank, end of the scalpel blade is lifted away from the tang's shoulder. The bending torsion induced in the scalpel blade acts against the grooves of the tang, including at the location of the detents of the scalpel blade's central aperture. In sliding the scalpel blade along the tang's grooves the blade's detents, which are square-shouldered and square-cornered, scrape against the tang's grooves. This is especially true just as the narrower forward portion of the scalpel blade's apertures is about to be slid clear of the grooves. The scraping makes the sliding extraction of the scalpel handle from the scalpel blade require modest manual force, and to thusly be difficult of being precisely manually controlled. The sudden release of spring force when the bent scalpel blade is pulled clear of the grooves of the tang of the scalpel handle is similarly difficult of being precisely manually controlled. This difficulty in positively controlling a sharp and dangerous object is problemsome.

For example, it is possible to remove a scalpel blade from a scalpel handle by simple manual manipulations. The rear end of the slot of the scalpel blade is typically disengaged from the shoulder of the tang of the handle by using surgical forceps to grasp the blade. The blade is bent by the forceps and slid along the tang. The required bending of the blade causes the blade to snap upwards when it reaches the wide portion of its variable-width slot. This action is dangerous because control of the scalpel blade with the forceps may be lost, and the blade may fly through the air and cut someone. Even if the flying blade does not cause injury, is simply propelled away from the removal area, it spreads contamination. It may become temporarily lost, and will ultimately have to be retrieved.

Because of the high risk of exposing people to injury, infection, or disease by unsafe scalpel blade removal and handling until proper disposal can be made, members of surgical staff are reluctant to use forceps or hemostats to remove scalpel blades because, if their hands slip along the blade or if they lose control of the blade, they or other personnel may be cut. The recent outbreak of the highly contagious AIDS disease has further highlighted the need for a safe way of removing and disposing of used scalpel blades.

A number of previous scalpel blade removers and disposal devices attempt to deal with the requirement for safe removal and disposal of used scalpel blades. For example, U.S. patent Ser. No. 4,106,620 discloses the use of an internally notched retaining device for the dispensing of surgical scalpel blades. The surgical blade and the tang of the scalpel handle are inserted into a cavity of the device through a small hole. The handle is then manipulated, with some difficulty, so that the rear end of the scalpel blade slips between outwardly projecting ears of the retaining device. The handle is then manipulated to lift the rear portion of the tang away from the rear portion of the scalpel blade's aperture and to withdraw the tang from the scalpel blade's aperture.

A SCALPEL BLADE REMOVER AND COLLECTOR shown in U.S. patent Ser. No. 4,168,777 requires that the scalpel handle should be precisely aligned with the body of a blade removing/receiving device in order to ensure that the edge of the shank of the scalpel blade properly engages a flange which retains the blade as the scalpel handle is withdrawn.

U.S. patent Ser. No. 4,318,473 for a SURGICAL BLADE REMOVER AND DISPOSAL DEVICE likewise requires that, a tang mounting a scalpel blade having been inserted into a blade receiving/disposing device, the handle must be moved in order to bow the blade and to release a the blade from the tang so that the handle may be withdrawn.

Still another mechanism is taught in U.S. patent Ser. No. 4,746,016 for a BLADE REMOVAL AND/OR MOUNTING MECHANISM AND DISPENSER EXTRACTOR-DISPOSAL APPARATUS INCLUDING SAME. The mechanism includes a handle guide on one side of a passageway and an extracting means affixed on the opposite side of the passageway. The handle guide permits deflection of the handle for withdrawal of the tang out of a mating relationship with the elongated slot of the scalpel blade, which is retained within the mechanism by the blade retaining means.

The previous mechanisms that act to remove a scalpel blade from a scalpel handle by sticking the blade mounted upon the handle's tang into a cavity and by subsequently maneuvering the handle in order to dislodge the blade do not work well because of the forces required, and because of the nonspecific and uncontrolled nature of the force application. This limitation on this class of previous devices is, to some extent, obvious. A scalpel blade mounted to a scalpel handle is intended to be inserted into bodily cavities, including into bone, without coming loose from the handle. Although the various removal mechanisms that are directed to dislodging scalpel blades from scalpel handles exhibit internal contours that are more effective to so dislodge the blades from the handles than are bodily cavities, they are generally inefficient and ineffective in operation.

Possibly because of the operative limitations of that class of prior scalpel blade removal devices wherein the scalpel handle is maneuvered to dislodge the scalpel blade, some scalpel blade removal devices employ moving parts to attempt to remove the scalpel blade from the scalpel handle.

For example, U.S. patent Ser. No. 4,386,457 shows an SURGICAL BLADE REMOVER-RECEPTACLE including a housing having an aperture. A scalpel blade attached to a tang of a scalpel handle is inserted into the aperture. The scalpel handle's tang is pressed downwards into a narrow notch in the wall surrounding the aperture so that the edges of the notch engage the shank of the scalpel blade, preventing it from being moved into the notch. If this was all that was used for attempting to separate the scalpel blade from the scalpel handle, than this particular remover-receptacle would be substantially similar to previous devices. However, two spring-loaded pinch members extend from within the aperture. These pinch members are pinched together by the finger of a user so as to engage the proposed edges of the blade, effectively preventing it from moving as the scalpel handle is disengaged from the scalpel blade and pulled away from the remover-receptacle. When the pinch members are released, the blade falls to the bottom of the interior of the housing, which serves as a receptacle.

Likewise, U.S. patent Ser. No. 4,730,376 for a BLADE REMOVAL APPARATUS FOR CHANGEABLE BLADE SCALPEL shows a box having a receptacle for a scalpel blade mounted to a scalpel handle. When the scalpel blade on the handle's tang is located within the box, a pair of projection pieces on the box force the blade surface located on both sides of the blade away from the undercut grooves of the handle's tang, thereby permitting the handle to be withdrawn. This forcing of the scalpel blade may induce by some movement of the scalpel handle (which is supposed to be fixedly held but is difficult to so hold), thereby permitting an undesirable uncertainty and variation in the extraction process.

This second class of previous scalpel blade removers are still generally characterized by the application of force between the scalpel blade handle, which is held in the hand, and the scalpel blade remover. In this manner, all the previous scalpel blade removers are simply substituting for the forces that were previously applied by forceps or hemostats.

The present invention will be seen to be considerably different. A scalpel blade attached to a scalpel handle will be seen to be inserted within the aperture of a removal/disposal device. Once so inserted, however, no forcing of the handle is required. Indeed, the scalpel blade will be removed from the handle so adroitly that the handle will simply fall away from the remover by force of gravity should the remover and handle be so spatially oriented This type of positive, certain, and controlled application of force is alien to the previous scalpel blade remover devices.

In another matter, there is a requirement of accountability of surgical instruments to ensure that none remain within the patient after surgery. It is desirable that, after removal, a used scalpel blade should be placed in a disposal unit that permits, and preferably supports, that an accounting can be made of the number of disposed blades which, when added to the number of unused blades, should equal the number of new blades brought into the surgery. U.S. patent Ser. No. 4,013,109 discusses some of these requirements.

Insofar as is possible, it is desired that the disposal apparatus for scalpel blades should facilitate, and not merely not impede, the accountability requirement. One good way of doing so would be to make it very difficult that the number used scalpel blades should be in any way miscounted by making it absolutely unambiguous as to the location of each and every such used blade.

Finally, a scalpel blade disposal apparatus should present a mechanically and biologically sound container for the necessary handling and transport, and ultimate disposal, of a biologically contaminated article. Along these lines, it is desired that the scalpel blade, or any biological contaminants thereon, should not readily be able to exit the disposal apparatus at any time during or after the disposal process.

Nonetheless to meeting all these requirements, it is desirable that a scalpel blade remover should be simple and fool proof in operation by people of all levels of strength, training, and prior familiarity with the remover and its operation. The remover should preferably reinforce its correct operation without permitting any substantial possibility of misuse Finally, a scalpel blade remover would preferably be inexpensive in construction, and completely disposable.

SUMMARY OF THE INVENTION

The present invention contemplates a one-time-use scalpel blade remover-receptacle. The remover-receptacle may be (i) used one time only in removing a scalpel blade from a scalpel handle, and (ii) is positive-acting in enforcing such one time use.

In particular, the remover-receptacle has a cavity and an opening to the cavity. The cavity accommodates a scalpel blade that is inserted through the hole while mounted to the tang of a scalpel handle. A blade removal mechanism moves unidirectionally relative to cavity for removing the scalpel blade from the tang of the scalpel handle while both the blade and the tang reside within the cavity.

The same mechanism that effects the removal simultaneously shuts, and thereafter maintains shut, the opening of the cavity to an extent sufficient so that (i) the tang of the scalpel handle may freely exit the cavity of the remover-receptacle, but (ii) the removed scalpel blade cannot exit the cavity of the remover-receptacle. Furthermore, (iii) no further scalpel blade, whether mounted to the tang of a scalpel handle or not, can thereafter be inserted into the cavity.

The removed scalpel blade is typically visible through a viewing port when contained within the cavity of the shut remover-receptacle. The scalpel blade remover-receptacle is thus (i) strictly one-time-use, (ii) operative under an uncircumventable protocol to ensure exactly one use, and only one use, and (iii) clearly and unambiguously visually observable to have either have been used, or not used, the one time.

The present invention further contemplates a scalpel blade remover-receptacle that bends a scalpel blade precisely in order to remove it from a scalpel handle. The remover-receptacle bends a scalpel blade, having an aperture presenting detents, from its locked position on a blade-retaining projection at the tang of a scalpel handle by action of (i) holding the blade in some regions, and (ii) bending it in other regions in a precise arc. The holding and bending of the scalpel blade is so precise that the scalpel handle may not only be reliably and freely withdrawn from the blade, but will actually fall away from the blade under force of gravity if so spatially oriented. The holding and bending of the scalpel blade is so steady and secure that even a scalpel blade that is broken at the region of its central aperture—a common failure location—can readily be removed from its mounted position on a scalpel handle.

The scalpel blade remover-receptacle so accomplishing the precision bending of a scalpel blade to permit its removal from its mounted position upon the tang of a scalpel blade handle includes two members spaced to form a channel. The members have distal (towards the point of the scalpel blade) and proximal (towards the shank of the scalpel blade) ends. The distal end regions of the two members are mutually shaped and spaced apart so as to form within a corresponding distal end region of the channel a blade-receiving surface that accepts the width and the breadth of the scalpel blade up to a position proximal along the scalpel blade from its aperture's detent. The scalpel blade is thereby held substantially planar at its distal end region.

A first one of the two members that is disposed upon the same side of the channel as the blade-retaining projection on the tang of the scalpel handle has, at a position proximate to a proximal end region of the channel, a recess. This recess is capable of receiving the proximal end region of the scalpel blade.

Meanwhile, the other, second, one of the two members—disposed on the opposite side of the channel to the blade-retaining projection on the tang of the scalpel handle—has a camming surface. This camming surface may be unidirectionally moved under manual squeezing force from lesser to greater proximity to the proximal end region of the channel, the proximal end region of the scalpel blade, and the recess of the first member. The camming surface is preferably hinged for this movement.

Movement of the second member's camming surface (i) serves to pressure the scalpel blade to bend in its region that is proximal from a position along the blade that is itself proximal to the aperture's detents into the first member's recess, while simultaneously (ii) fitting around the handle's tang so that the tang is not contacted or pressured. The bending of the scalpel blade in its proximal region while its distal region is held planar permits withdrawal of the handle from between the two members, and away from the bent scalpel blade, with essentially zero withdrawal force, thereby disengaging the scalpel blade from the scalpel handle and encapsulating it within the remover-receptacle.

These and other aspects and attributes of the present invention will become increasingly clear upon reference to the following drawings and accompanying specification.

DETAILED DESCRIPTION OF THE INVENTION

The present invention is embodied in an inexpensive and disposable scalpel blade remover-receptacle device. The device is typically molded entirely of plastic, typically polypropylene of yellow or orange color and ASTM R-93 hardness.

The scalpel blade remover-receptacle is directed to realizing at least two goals. First, a surgical scalpel blade will be removed from its mounted position upon the tang of a scalpel handle in a positive, effective, and efficient manner. The scalpel blade mounted upon the tang of a scalpel handle is inserted through a hole into a cavity of the scalpel blade remover-receptacle. A hinged member of the scalpel blade remover-receptacle is depressed under moderate force to bend the scalpel blade precisely and thereby permit the scalpel handle to be withdrawn with essentially zero force.

Second, the scalpel blade remover-receptacle remains, after actuation of its hinged member to effect the removal of a scalpel blade from a scalpel handle, in a permanently closed position encapsulating the removed scalpel blade. The remover-receptacle cannot normally be opened so as to permit access to, or egress of, the contained scalpel blade. Neither can another scalpel blade be inserted, whether affixed to the tang of a scalpel handle or not. The used and removed scalpel blade is visible through a viewing aperture. Accordingly, it is always known that each closed, and locked, scalpel blade remover-receptacle contains one, and exactly one only, scalpel blade.

Figure 1:
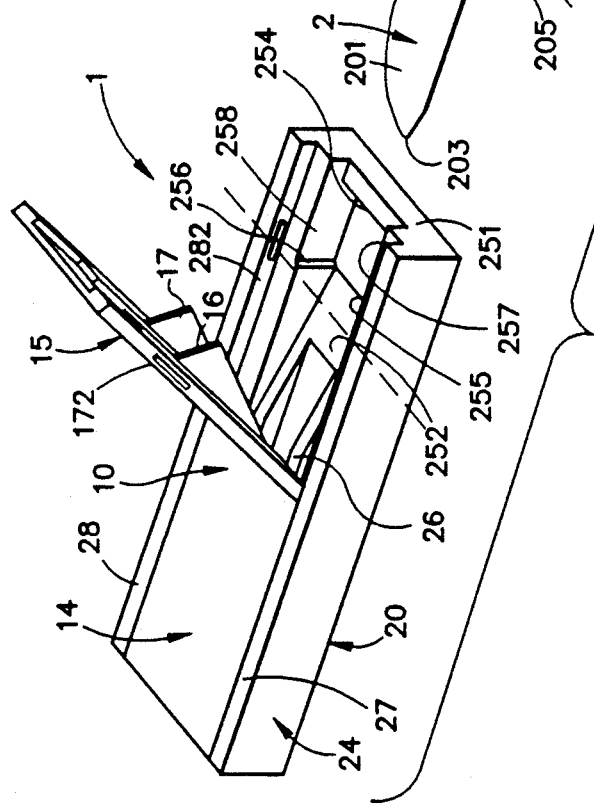
FIG. 1 is a perspective view of the preferred embodiment of a scalpel blade remover-receptacle in accordance with the present invention.

A perspective view of a preferred embodiment of a scalpel blade remover-receptacle 1 in accordance with the present invention is shown in FIG. 1. Side plan views are shown in FIG. 2 and a laid-open plan view in FIG. 3. The remover-receptacle 1 consists of an upper member 10 and lower member 20. Both members 10, 20 are normally molded integrally, and are normally connected when originally molded at their distal end walls 11, 21. After molding the members 10, 20 are aligned relative to each other in the indicted manner and are pressed together, thereafter forming a unitary assembly.

The lower member 20 is typically formed in the shape of a broad U-channel with short and thick side walls 27, 28. The lower member 20 possesses features, normally at the interior sides of both side walls 27, 28 to its central U-channel, that permit it to lock, separately and at different times, with each of the distal end section 14 and the proximal end section 15 of upper member 10. These locking features are typically configured as cavities 271 and 272 in sidewall 27, and symmetrical cavities 281 and 282 in opposite sidewall 28. Each of the cavities 271, 272, 281, 282 is complementary in shape to corresponding projections, or tabs, 171 and 172 on one side edge, and 181 and 182 on the opposite side edge, of upper member 10. All projections and cavities fit together tightly by elastomeric forces arising from the preferably plastic construction of members 10, 20. Upon initial assembly the distal end section 14 of upper member 10 is looked into the corresponding distal end section 24 of lower member 20 by engagement of cavity-and-tab pairs 271-171 and 281-181. At a later time the operation (to be discussed) of the remover-receptacle 1 will permit proximal end section 15 of upper member 10 to lock to corresponding proximal end section 25 of lower member 20 by engagement of cavity-and-tab pairs 272-172 and 282-182.

When the members 10, 20 are initially connected in their distal sections 14, 24 only, a flange, or tab, 12 of upper member 10 fits within a complementary cavity 22 of lower member 20. One purpose of tab 12, besides serving to interlock upper member 10 to lower member 20 and to maintain both such members 10, 20 in fixed relationship, is to serve as a safety stop to the distal end region 31 of cavity 30 formed between upper member 10 and lower member 20. When a scalpel blade 2 (shown in FIG. 2) is inserted within distal end region 31 of cavity 30, tab 12 will help to prevent that such scalpel blade should, under inadvertent high force, completely penetrate through the end wall 241 of cavity 30, and at the distal end section 24 of the lower member 20 of remover-receptacle 1 (which is typically made of plastic), to protrude from distal end walls 11, 21.

The lower member 20 presents a shaped cavity, or recess, 34 in its proximal end section 25 proximate its proximal end wall 251 and adjacent the proximal end region 32 of central cavity 30. Indeed, recess 34 is, over some of the extent of cavity 30, integral with cavity 30. The lower member 20 presents, as one boundary of its recess 34, an angled slope 252. This angled slope 252 proceeds from a region deep within lower member 20 and proximate its outside surface 253 to a ledge, or lip, 26 that is proximal to the center point (near shoulders 33) within cavity 30, and to the hinge 13 to upper member 10. The precise location of this ledge 26 will prove to be important in the precision bending of the scalpel blade 2 (shown in FIG. 2) by the remover-receptacle 1.

The recess 34 to lower member 20 also presents an end wall 254 that is complementary to the shank end 204 of scalpel blade 2. This end wall 254 will be seen to be a stop to scalpel blade 2 during its removal from scalpel handle 3. The angling of the end wall 254 relative to the longitudinal axis of the remover-receptacle 1, the scalpel blade 2, and the scalpel handle 3, precludes that any rotational torque will be induced on scalpel blade 2 during its removal.

The upper member 10 is divided into a distal end section 14 that is connected to a proximal end section 15 by a hinge 13. The distal end section 14 is fixedly mounted to lower member 20, and, with such lower member 20, defines the distal end region 31 of cavity 30. This distal end region 31 to cavity 30 is shaped, and spaced apart, so as to accept the width, breadth, and contour of a scalpel blade 2 (shown in FIG. 2) up to a position proximal along the scalpel blade 2 from the detents 205 of its aperture 206. To facilitate that the distal end region 201 of scalpel blade 2 will be snugly held planar when inserted into distal end region 31 of cavity 30 (as illustrated in FIGS. 2b-2e), the lower side of the distal end section 14 of upper member 14 presents two longitudinal rails 141, 142. These rails 141, 142 press the scalpel blade 2, under elastomeric force arising from the plastic construction, tightly against the flat upper surface 242 of distal end section 24 of lower member 20, holding the inserted scalpel blade 2 securely. Overall, the distal end region 31 of cavity 30 fits the distal end region 201 of scalpel blade 2 snugly.

The proximal end section 15 of upper member 10 mounts at its lower surface two projections 16, 17. The projections 16, 17 are spaced apart in a direction transverse to the longitudinal axis of remover-receptacle 1 by a separation sufficient to accommodate the width of the tang 301 to scalpel handle 3. The projections 16, 17 are angled so that when proximal end section 15 of upper member 10 is pressed downwards against lower member 20 so as to form a plane that is coextensive over the upper surfaces of both the distal end section 14 and the proximal end section 15 of upper member 10 (as illustrated in FIGS. 2d and 2e), then this surface will be roughly parallel to, and slightly spaced apart from, the angled slope 252 of lower member 20 (best shown in FIG. 2e). The proximal end section 15 of upper member 10 is hinged for movement relative to distal end section 14 of upper member 10, and relative to lower member 20, by hinge 13.

The remover-receptacle 1 is variously sized so as to be adapted to standard size and configuration scalpel blades 2 and scalpel handles 3. There are both (i) small and (ii) large size scalpel blade handles 3. Moreover, these handles vary slightly depending upon whether of U.S. or foreign, primarily Pakistan, manufacture. The standard scalpel blade handle 3 dimensions (in inches) are as follows:

|  | A | B | C | D | E |
|---|---|---|---|---|---|
| Large (US) | .124 | .140 | .385 | .179 | 1.190 |
| Small (US) | .113 | .093 | .384 | .166 | .830 |
| Large (Pakistan) | .131 | .141 | .387 | .154 | 1.190 |
| Small (Pakistan) | .106 | .091 | .352 | .113 | .830 | where dimension A is the thickness of the tang 301 and dimension B is the thickness of the handle 3, where dimension C is the width of the tang 301 and dimension D is the width of the handle 3, and where dimension E is the length of the tang 301. Of these dimensions, A and B and E are most important to the sizing of remover-receptacle 1. The remover-receptacle 1 is preferably made in two sizes—small and large—which respectively function for correspondingly-sized small and large scalpel blades mounted on all handles The manner of extracting a scalpel blade 2 from a scalpel handle 3 with the scalpel blade remover-receptacle 1 in accordance with the present invention is illustrated by steps in FIG. 2, consisting of FIG. 2a through FIG. 2e. Beginning with FIG. 2a, a scalpel handle 3 mounting a scalpel blade 2 on its tang 301 is slid in the indicated direction and orientation into the open end of central cavity 30 of remover-receptacle 1.

Figure 2A:
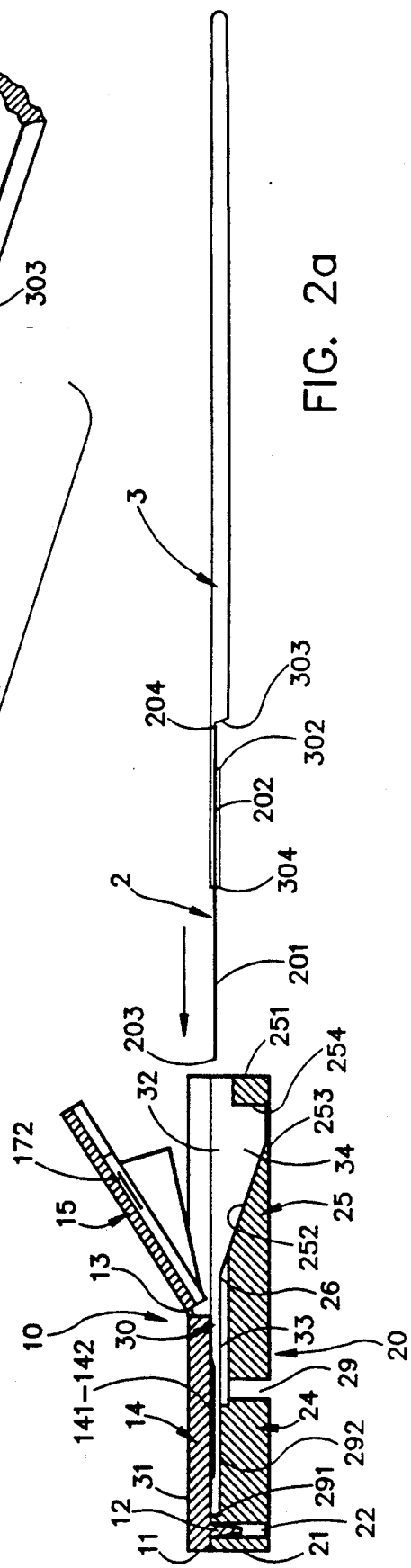
FIG. 2, consisting of FIG. 2a through FIG. 2e, are sectional views showing the operation of the preferred embodiment of the scalpel blade remover-receptacle in accordance with the present invention for removing a scalpel blade from a scalpel handle.
Figure 2B:
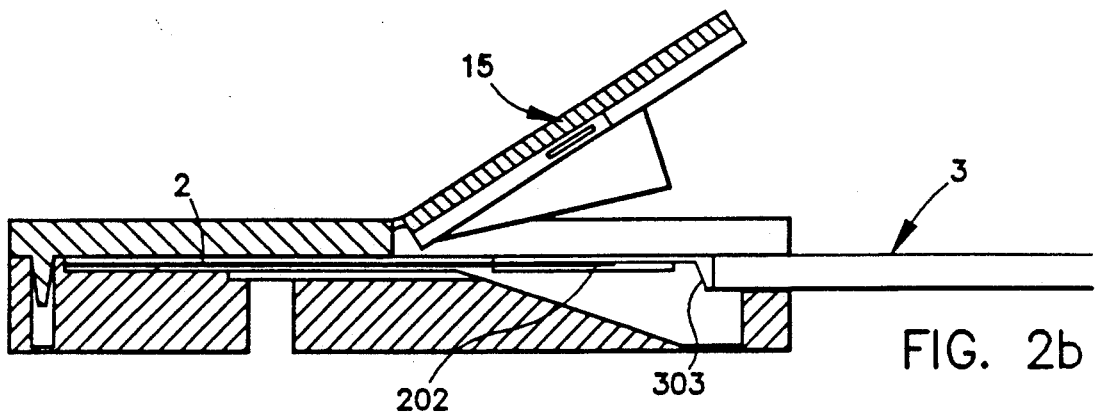
Figure 3:
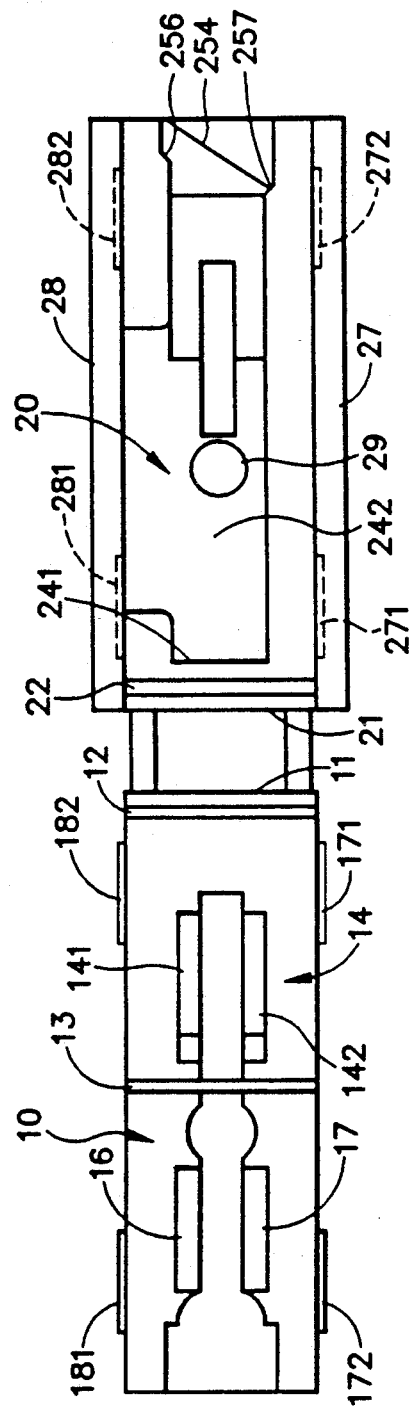
FIG. 3 is a cross-sectional plan view of the preferred embodiment of the scalpel blade remover-receptacle in accordance with the present invention laid open to expose the interiors of both its upper and lower members.

The scalpel blade 2, and scalpel handle 3, come to assume the fully seated position wherein the tip 203 of scalpel blade 2 is spaced apart from the tab 12 of upper member 10, all as shown in FIG. 2b. The scalpel blade 2 mounted to scalpel handle 3 is stopped at its inserted position in cavity 30 by left and right shoulder stops 255, 256 located on the side walls 257, 258 of the proximal end region cavity 31 lower member 20. These two shoulder stops 257, 258 contact the scalpel blade handle 3 at its region of increased width 303.

The thickness of cavity 30 abruptly narrows at location 33. The rails 141, 142 of the upper member 10 draw proximate to the upper surface of the lower member 20 at this location 33, abruptly decreasing the thickness of cavity 30 and abutting the distal end 304 of the tang 301 of scalpel blade handle 3. This region of reduced thickness further prevents that the scalpel blade 2 should move any further distally into cavity 30 than is shown.

Notably, both the stops 255, 256 and the narrowing thickness at location 33 act against the scalpel handle 3, and not against the scalpel blade 2, which may be of varying size and contour.

In its inserted position the entire distal end region 201 of scalpel blade 2 is substantially tightly enclosed by the distal end region 31 of cavity 30. The ledge 26 of the angled slope 252 to proximal end section 25 of lower member 20 contacts the scalpel blade 2 at a position proximal along the scalpel blade 2 from the detents 205 of its aperture 206. The distal end section 201 of scalpel blade 2 is thus held substantially planar, and unmoving.

Figure 2C:
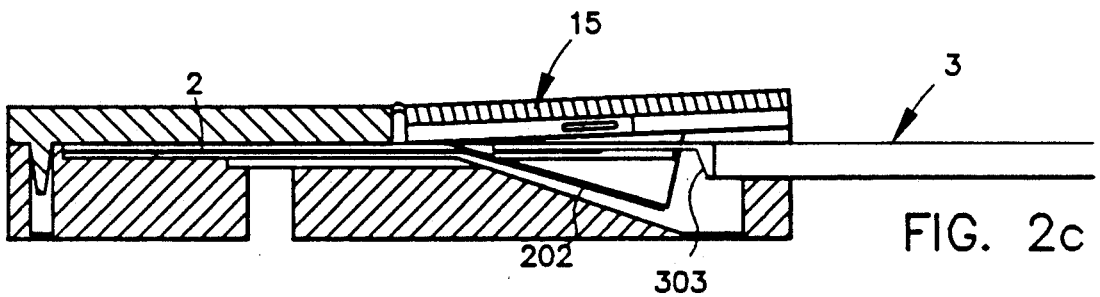
Figure 2D:
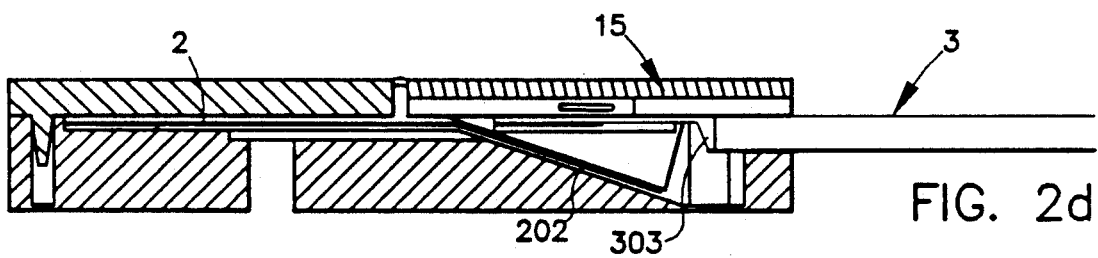
Figure 2E:
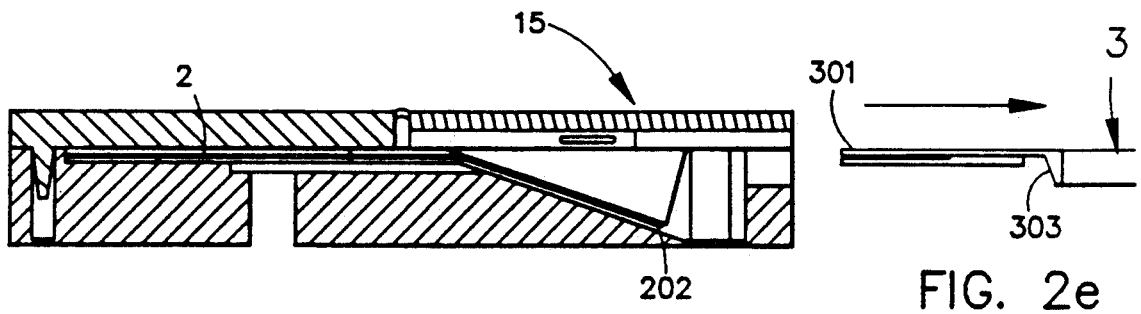

While the scalpel blade 2, and scalpel handle 3, are lodged as illustrated in FIG. 2b within the remover-receptacle 1, the hinged proximal end section 15 of upper member 10 is depressed towards lower member 20, such as by squeezing force between the thumb and fingers, as illustrated in the sequence from FIG. 2b to FIG. 2d. By act of this hinged movement of proximal end section 15 relative each of to the proximal end region 32 of cavity 30, recess 34 of lower member 20, and proximal end section 202 of scalpel blade 2, the scalpel blade 2 is bent in its proximal end section 202 in a very precise manner.

As is most particularly illustrated in FIG. 2c and FIG. 2d, the projections 16, 17 of upper member 10 force the proximal end section 202 of scalpel blade 2 away from the proximal end retaining lip, or edge, 302 to tang 301 of scalpel blade handle 3. The proximal end section 202 of scalpel blade 2 is bent, as is most particularly illustrated in FIG. 2d, so that it is smoothly and completely freed from lip 302 of tang 301, thereby permitting that the tang 301 may be extracted from the central aperture 206 of the scalpel blade 2.

It is important to understand that if the scalpel blade 2 was being removed by hand, or by previous scalpel blade remover devices, then the bending of its proximal end section 202 would cause the detents 205 of the central aperture 206 of scalpel blade 2 to scrape against the edge grooves 305 of the tang 301. This scraping force between the square shoulders of the scalpel blade's detents 205 makes sliding such tang 301 relative to the scalpel blade 2 difficult, and, when the tang 301 passes the detents, dangerous in the release of stored spring forces.

In accordance with the present invention, the production of any strong forces between the detents 205 (that occur at the transition from the broad to the narrow region of the central aperture of the scalpel blade 2) and the tang's channels, or grooves, 305 is precluded. Because these forces are precluded, there is no sudden release of energy when the tang 301 is withdrawn from the central aperture 206 of scalpel blade 2. Indeed, there is no force on tang 301 at all. The buildup and release of forces is precluded by the fact that the distal end region 201 of scalpel blade 2 is constantly held tightly, and substantially planar, in the distal end region 31 of cavity 30. The scalpel blade 2 is so held planar from a position that is proximal of the detents 205 of its central aperture 206. The scalpel blade's detents 205 do not move during extraction of the scalpel blade handle 3 from the scalpel blade 2, and do not preclude such extraction.

The final extraction of the scalpel handle 3 from the scalpel blade 2, which is left encapsulated within the cavity 30 of remover-receptacle 1, is shown in FIG. 2e. The scalpel handle 3 slides in the indicated direction from the remover-receptacle 1, and from the scalpel blade 2, with essentially zero removal force. If the remover-receptacle 1 is tilted so that the scalpel handle 3 is downwards, then it will fall from the remover-receptacle 1 under force of gravity. The scalpel blade 2 is, of course, tightly retained (in its bent position) within the remover-receptacle 1, and will not exit such remover-receptacle 1 in any orientation thereof.

The close holding and precise bending of the scalpel blade 2 is very well balanced, and nothing tends to skew or jam. As proof of this assertion, a scalpel blade that is broken in diverse regions, including in its regions adjacent its central aperture, may still be reliably removed by remover-receptacle 1.

The scalpel blade remover-receptacle 1 also works well with new-type "strong back" scalpel blades that exhibit a raised ridge opposite the cutting edge. Operating on scalpel blades of varying thickness is facilitated by rails 141, 142. Finally, the scalpel blade remover-receptacle 2 works scalpel blades number 12, which exhibits a hook structure.

The removed scalpel blade 2 encapsulated within the cavity 30 of the remover-receptacle 1 is clearly visible through viewing aperture 29 of lower member 20. This viewing aperture 29 may be a simple hole or may be a transparent area, normally of clear plastic. A scalpel blade remover-receptacle 1 can be closed, and locked closed, without the presence of a scalpel blade 2 therein. However, such a used remover-receptacle 1 will not show the presence of a scalpel blade 2 through the viewing aperture 29.

In its closed position, the scalpel blade remover-receptacle 1 cannot readily be reopened The proximal end section 15 of upper member 10 is held in its down-locked and closed position by tabs 172, 182 of upper member 10 which engage and lock complementary cavities 272, 282 within lower member 20. Although the scalpel blade remover-receptacle can be pried apart in an emergency, the cavity-and-tab locks 272-172 and 282-182 are intended to keep it tightly closed. The scalpel blade 2 is normally transported, and disposed of within a furnace, while it is securely retained within remover-receptacle 1.

Although contaminated fluids can leak from the cavity 30 of the remover-receptacle 1, many fluids are subject to collect in the convolute contours, including in recess 34, of such remover-receptacle. Normally if the remover-receptacle 1, with a contaminated removed scalpel blade 2 contained therein, is transported with some care then no material will be loosed from the interior of such remover-receptacle 1.

In accordance with the preceding discussions, certain adaptations and alterations of the present invention will suggest themselves to practitioners of the mechanical arts. For example, the moveable proximal end section 15 of upper member 10 need not have been hinged to distal end section 14 of such upper member 10. Rather, the proximal end section 15 could have been oppositely hinged at the proximal end of device 1 and its upper member 10. Still further alternatively, the proximal end section 15 need not have been hinged at all. It could, instead, ride within a channel between positions of relatively greater, and relatively lesser, extension from cavity 30, scalpel blade 2, and recess 34. In each of its different mountings the proximal end section 15 would be moved against the spring force of scalpel blade 2 so as to detach such scalpel blade 2 from the lip 302 of the tang 301 of the handle 3.

Accordingly, the present invention should be interpreted broadly, in accordance with the following claims, only, and not solely in accordance with that particular embodiment within which the invention has been taught.

What is claimed is:

1. A device for bending a scalpel blade, the scalpel blade having an aperture presenting detents, at and from its locked position on a blade-retaining projection at the tang of a handle in order to remove the blade from the handle, the device comprising:

two members spaced to form a channel, the members having distal and proximal ends;

the distal end regions of the two members mutually shaped and spaced apart so as to form within a corresponding distal end region of the channel a blade-receiving surface that accepts the width and the breadth of the scalpel blade up to a position proximal along the scalpel blade from its aperture's detents in order to hold the distal end region of the scalpel blade substantially planar;

a first one of the two members that is disposed on the same side of the channel as the blade-retaining projection on the tang of the handle having at a position proximate to a proximal end region of the channel a recess that is capable of receiving the proximal end region of the scalpel blade;

the other, second, one of the two members that is disposed on the opposite side of the channel to the blade-retaining projection on the tang of the handle having a camming surface that may be moved from lesser to greater proximity to the proximal end region of the channel, to the proximal end region of the scalpel blade, and to the recess of the first member;

the second member's camming surface serving to pressure the scalpel blade to bend in its region that is proximal from a position along the blade that is itself proximal to the aperture's detents into the first member's recess while simultaneously permitting that the handle's tang should not be substantially pressured; and interlock means, between the moving camming surface of the second one of the two members and the first one of the two members, for locking the moving camming surface in its position bending the scalpel blade and disengaging the handle;

therein disengaging the scalpel blade from the handle to that the handle is withdrawable from the two members, and from the bent scalpel blade within the channel, without any appreciable scraping frictional force between the scalpel blade aperture's detents and the tang of the handle.

2. The blade-bending scalpel blade remover device according to claim 1 wherein the interlock means comprises:

complementary projections and recesses that lock together and that, once locked, are not readily subject to being unlocked.

* * * * *